United States Patent [19]

Ushiyama et al.

[11] Patent Number: 4,605,548
[45] Date of Patent: Aug. 12, 1986

[54] DRUG ADMINISTRATION MATERIAL

[75] Inventors: Keiichi Ushiyama; Hisashi Ichinose, both of Osaka, Japan

[73] Assignee: Nitto Electric Industrial Co., Ltd., Osaka, Japan

[21] Appl. No.: 632,149

[22] Filed: Jul. 18, 1984

Related U.S. Application Data

[60] Division of Ser. No. 498,680, May 31, 1983, abandoned, which is a continuation of Ser. No. 288,957, Jul. 31, 1981, abandoned.

[51] Int. Cl.$^4$ .................... A61L 15/03; A61K 9/24
[52] U.S. Cl. ..................................... 424/15; 424/16; 424/20; 424/21
[58] Field of Search .................. 424/15, 16, 20, 21

[56] References Cited

U.S. PATENT DOCUMENTS 4,292,299  9/1981  Suzuki et al. .................. 424/21

Primary Examiner—John Kight
Assistant Examiner—M. L. Moore
Attorney, Agent, or Firm—Sughrue, Mion, Zinn, Macpeak & Seas

[57] ABSTRACT

A drug administration material for continuously administering an active drug at a controlled rate through an integument or mucous membrane, which comprises a drug-retaining layer having provided on at least one side thereof a drug administration layer which continuously feeds an active drug to an integument or mucous membrane, said drug administration layer comprising a porous membrane containing in pores thereof a liquid having a limited solubility for the active drug.

4 Claims, 2 Drawing Figures

DRUG ADMINISTRATION MATERIAL

This is a division of application Ser. No. 498,680, filed May 31, 1983 which is a continuation of application Ser. No. 288,957 filed July 31, 1981 now abandoned.

FIELD OF THE INVENTION

This invention relates to a drug administration material enabling constant and continuous administration of an active drug, generally or locally, through integument or mucous membrane, and to a process for preparing such.

BACKGROUND OF THE INVENTION

General or local administration of an active drug through integument or mucous membrane is usually conducted by applying thereto a solution of a drug in a solvent, by applying as a creamy ointment obtained by mixing a drug with a soft material, or by inserting or embedding such in the form of suppository or tablet.

One of the inevitable defects with these administration methods is that, though the drug level in a circulatory system is raised each time a drug is administered, the drug level in blood or in a particular part of body decreases in a short time, thus being not maintained at a constant level.

In order to solve this defect, approaches have been developed for continuously administering an active drug, generally or locally, through integument or mucous membrane, which have been attempted to be practiced.

One of such approaches is a pressure-sensitive, adhesive administration tape or film which comprises a carrier having provided thereon a pressure-sensitive, adhesive composition containing an active drug added thereto. This administration tape or film enables continuous administration of the active drug, because the adhesive composition effectively prevents the drug from being released onto the skin surface all at one time. However, the quantity of the administered drug decreases with time. Thus such tape or film fails to continuously administer the drug at a constant rate.

Another approach is a drug administration material comprising a stratum consisting of a backing material, a drug-retaining layer, a polymeric film layer which controls a drug migration rate, and a pressure-sensitive, adhesive layer. This material allows a drug contained therein to diffuse and permeate through the polymeric film layer and the pressure-sensitive, adhesive layer to the skin surface. However, since control of the drug diffusion and migration rate is conducted by controlling the diffusion rate in the polymeric material, additional factors are involved which control permeation of the drug in both the polymeric film and the adhesive layer. Thus, the kinds of the polymeric material and the adhesive must be properly selected depending upon the structure of a drug, and also with consideration for the adhesiveness of the adhesive to skin. Such complexity with the drug administration material has made the application of such to various drugs difficult.

SUMMARY OF THE INVENTION

This invention provides a drug administration material for administering a drug continuously and constantly, which enables administration of an active drug released from a drug-retaining layer of the drug administration material through integument or mucous membrane using a drug administration layer comprising a novel porous membrane whose pores are filled with a liquid having a limited solubility for the drug.

More particularly, the present invention provides a drug administration material useful for administering an active drug continuously at a constant rate through integument or mucous membrane, which comprises a drug-retaining layer having provided on at least one side thereof an administration layer capable of supplying an active drug continuously to integument or to mucous membrane, said administration layer comprising a porous membrane and a liquid which is filled in the pores of the membrane and has a limited solubility for the drug.

BRIEF DESCRIPTION OF THE DRAWINGS

In FIGS. 1 and 2, numeral 1 designates a drug administration material, 11 a drug-retaining layer, 12 a drug administration layer, and 3 an adhesive piece.

DETAILED DESCRIPTION OF THE INVENTION

One embodiment of the present invewntion comprises a sheet- or film-shaped drug-retaining layer composed of a mixture of a material allowing an active drug to diffuse and permeate therethrough and an active drug, and an administration layer comprising a porous membrane, containing a liquid filling the pores of the membrane, said liquid having a limited solubility for the active drug, and said drug-retaining layer and said administration layer being intimately superposed one over the other.

The liquid constituting the administration layer dissolves an active drug that has diffused and permeated through the drug-retaining layer onto the surface of the drug administration layer in a definite quantity, i.e., up to saturation, and in turn supplies the active drug to the opposite side of the administration layer, in contact with integument or mucous membrane, at a constant rate.

Accordingly, the porous membrane itself substantially functions merely as a retainer of the liquid.

Another embodiment of the present invention comprises a drug-retaining layer composed of a mixture of a material which is viscous at ordinary temperatures and an active drug and an administration layer. A backing sheet or film protecting the surface of the drug-retaining layer is formed on the administration layer, on the opposite side from the drug-retaining layer.

A further embodiment of the present invention comprises a drug-retaining layer prepared by impregnating an active drug in a porous sheet or film and a drug administration layer. The drug in the drug-retaining layer migrates to the interfacial portions with the drug administration layer due to a concentration gradient produced resulting from the drug administration.

A still further embodiment of the present invention comprises a drug-retaining layer comprising a porous membrane containing an active drug filled in the pores of the membrane and a drug administration layer.

Figure 1:
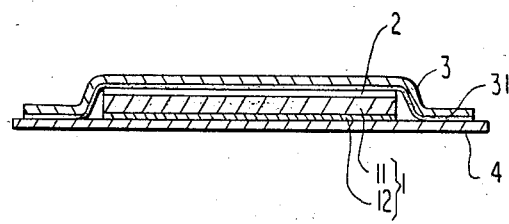
FIG. 1 is a sectional view showing one embodiment of a drug administration material of the present invention.

FIG. 1 shows a typical embodiment of the drug administration material of the present invention to be applied to integument, wherein a pressure-sensitive, adhesive film or sheet 3, of a size protruding preferably 10 mm or more from the edge of the administration material 1, is provided. By means of adhesive piece 3, consisting of a film 3 (for example, aluminum foil, polyethylene terephthalate film, polypropylene film, etc.), pressure-sensitive adhesive layer 31, and barrier layer 2, diffusion of active drug substantially does not occur from the surface of drug-retaining layer 11 of the drug administration material 1 comprising drug-retaining layer 11 and drug administration layer 12 (composed of a porous membrane containing a liquid having a limited solubility for a drug in the pores of the membrane), and delaminatable protective film 4 also prevents diffusion of the active drug, temporarily, until removed for use.

Figure 2:
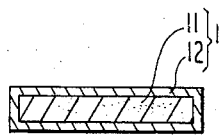
FIG. 2 is a sectional view showing another embodiment.

FIG. 2 shows a typical embodiment of the drug administration material to be applied to mucous membrane, wherein drug-retaining layer 11 is enclosed by drug administration layer 12 so that the layer 11 is tightly sealed by the layer 12 to form drug administration material 1.

The drug administration material of the present invention contains a generally or locally active drug and functions to feed the drug to a material-applied site or to a site distant from the material-applied site via blood to produce pharmaceutical effects.

The active drug to be used in the present invention is required to be absorbable through integument or mucous membrane as well as to be soluble in a liquid to be described hereinafter. A particular active drug is practically selected from those which are absorbed generally or locally to attain a desired pharmaceutical response.

Specific examples of suitable active drugs include: corticosteroids such as prednisolone, dexamethasone, fluocinolone acetonide, beclomethasone, betamethasone, etc.; analgesic antiinflammatory agents such as indomethacin, flufenamic acid derivatives, phenylbutazone, etc.; antibiotics such as erythromycin, chloramphenicol, cephalexin, tetracycline, etc.; agents acting on central nervous system such as barbiturates, diazepam, promazine, chloropromazine, meprobamate, etc.; cardiacs such as ajmaline, nitroglycerin, denitrosorbate, dipyridamole, etc.; antihypertensive agents such as reserpine, clonidine, etc.; and diuretic antihypertensive agents such as thiazides. These drugs may be used in combinations of two or more, if desired. The quantity of an active drug to be retained in the drug-retaining layer is decided for each drug depending upon the designed effect-lasting period, the drug-absorbing rate through skin, the metabolic rate, and the effective blood level of each drug.

The matrix of the drug-retaining layer which retains an active drug as described above in a predetermined quantity migrating through the drug administration layer in contact with the drug-retaining layer by being dissolved in a liquid constituting the drug administration layer, is constituted by a material(s) selected from the group consisting of those materials through which an active drug easily migrates by diffusion, those materials which are viscous at ordinary temperature, porous materials, and porous membranes.

Preferable examples of the materials to be used as a matrix for the drug-retaining layer allowing an active drug to diffuse and permeate therethrough include high molecular materials such as polyethylene vinyl acetate, polyvinyl alcohol, flexible polyvinyl chloride, flexible polyamide, polyolefin, polyacrylic resin, polyurethane resin, and thermosetting or room temperature vulcanization type silicone rubber.

Examples of materials that are viscous at room temperature (about 20° C.–30° C.) include viscous materials primarily comprising copolymers between (meth)acrylic esters (e.g., butyl (meth)acrylate, hexyl (meth)acrylate, 2-ethylhexyl (meth)acrylate, etc.) and monofunctional monomers (e.g., (meth)acrylic acid, hydroxyethyl acrylate, acrylamide, etc.) and/or vinyl monomers (e.g., vinyl acetate, acrylonitrile, etc.); rubbers (e.g., silicone rubber, polyisoprene rubber, styrene-butadiene (or isoprene)-styrene copolymer rubber, natural rubber, etc.); and synthetic resins (e.g., polyvinyl ether, polyvinyl alcohol, carboxymethyl cellulose, etc.).

The drug-retaining layer comprising a matrix of a material allowing an active drug to diffuse and permeate therethrough or of a material viscous at ordinary temperatures is constituted by such material containing an active drug uniformly mixed therein. When the concentration of the drug retained in the portion of the drug-retaining layer in contact with the drug administration layer is decreased as a result of migration of the drug through the drug administration layer, the drug dissolved in the other portions migrates through the drug-retaining layer by diffusion, due to the thus-produced concentration gradient in the matrix, to reach the interfacial portion between the drug-retaining layer and the drug administration layer for subsequent transfer to the drug administration layer.

Other materials to be used as the matrix for the drug-retaining layer are sheets or films of porous structure, for example, nonwoven fabric or paper (bases weight: 10 to 300 g/m$^2$) comprising synthetic fiber and/or natural fiber, woven fabric, knitted fabric, felt, mat (pad), and open cell foamed film or sheet.

In using these porous materials, an active drug is mixed with a suitable solvent or carrier, and the porous materials are dipped in the mixture or rubbed with such on one side or on both sides to thereby prepare a drug-retaining layer comprising such impregnated with the drug.

The porous membrane to be used in practicing the present invention constituting the drug administration layer is not particularly limited as to the kind of the membrane-forming material used, as long as it has physical or chemical penetration pores of preferably 10$\mu$ or less, practically 0.01 to 5$\mu$, in pore size. More preferably, those with a void space of at least 30% (by volume) are used, with those of 70% or more void space being more practical.

As the material for the membrane, ethylenepolyvinyl alcohol copolymer, cellulose acetate, polyamide, polyvinyl chloride, polyolefin, polyacrylonitrile, polysulfon, polyvinyl alcohol, polyimide, fluorine-containing resin, etc., are used. Preparation of such porous membrane using these materials is conducted by dissolving, for example, a polyacrylonitrile-containing copolymer in a solvent to prepare a thick solution, casting the solution onto a support, dipping such in a non-solvent to remove the solvent, heat-treating the thus-obtained membrane, and drying such at temperatures lower than the heat-treating temperature.

As will be described hereinafter, such porous membranes usefully function as a retainer of a liquid which transports a drug to integument or mucous membrane, also usefully functioning as a matrix retaining the drug.

The drug-retaining layer, wherein pores of the porous membrane are filled with drug itself or with a solution or a mixture of a drug in or with a liquid which facilitates migration of the drug and is incompatible with a solution controlling transportation of the drug to integument or to mucous membrane and which has a higher saturation solubility for the drug than such transportion-controlling liquid, has the advantages that it allows the drug to more freely migrate therethrough to the absorption layer as compared with the aforesaid drug-retaining layer comprising a mixture of two materials as a retaining matrix. Furthermore, as compared with the impregnation type drug-retaining layer using a porous material, the present drug-retaining layer causes less absorption of the drug onto the porous material itself, and produces less drug loss, because the drug in distant portions from the absorption layer can surely migrate to the absorption layer surface.

The pores of the thus-prepared porous membrane are filled with a liquid having a limited solubility for a drug, for example, by coating such or by dipping the membrane in such liquid. The liquid is stably retained in the membrane by capillary pressure, and thus the liquid-containing membrane can be used as a drug administration layer of the present invention.

Examples of the liquids which are to be filled in pores of the porous membrane and transport a drug in the drug-retaining layer to integument or mucous membrane include vegetable fats and oils (e.g., olive oil, salad oil, etc.), animal fats and oils (e.g., squalene, lanolin, lard, etc.), paraffins (e.g., liquid paraffin, vaseline, ozocerite, ceresine, gilsonite, etc.), polyhydric alcohols and the derivatives thereof (e.g., propylene glycol, ethylene glycol, polyethylene glycol, polypropylene glycol, glycerin, etc.), higher fatty acids and the derivatives thereof (e.g., stearic acid, myristic acid, palmitic acid, oleic acid, linoleic acid, sebacic acid, etc.), substantially non-volatile solvents (e.g., sulfoxides such as dimethyl sulfoxide and dimethylformamide, and amides such as dimethylacetamide, etc.), and the like. These liquids may be used in combinations of two or more, if desired.

The drug administration material of the present invention is used most conveniently in the form illustrated in FIGS. 1 or 2. It may be applied to the intended portion of a body by fixing with, for example, a bandage, or by using a double-coated tape which does not substantially inhibit diffusion migration of a drug which contains preferably a thin tough nonwoven fabric or Victoria lawn as a support.

The size of the material generally ranges from 1 to 100 cm$^2$, though depending upon the activity of an active drug retained therein and upon the intended pharmaceutical response.

The drug administration material of the present invention is significant in that the liquid contained in the drug administration layer is designed so that the liquid dissolves a drug coming into contact with the drug administration layer to feed the drug to integument or to mucous membrane. The liquid continues to dissolve the drug up to saturation, and after saturation stops dissolving the drug. When the drug administration material of the present invention is brought into contact with integument or mucous membrane and absorbed therethrough, the drug level in the liquid decreases from saturation. Then, the liquid again starts dissolving the drug, and while the material is applied to integument or to mucous membrane, the liquid continues to dissolve the drug until the drug is substantially exhausted from the drug-retaining layer. Thus the active drug is applied to integument or mucous membrane continuously at a constant rate.

The same drug can be absorbed through integument or through mucous membrane at a faster or slower rate as necessary by properly selecting liquids having different solubility for the drug.

The present invention is described in more detail by reference to following examples, which, however, are not to be construed as limiting the present invention.

EXAMPLE 1

1 mg of indomethacin was added to, and mixed with, 100 g of polyethylene vinyl acetate to obtain a 40 $\mu$ thick drug-retaining layer (containing 500 $\mu$g/cm$^2$ of indomethacin).

Separately, a polypropylene porous membrane having a thickness of 25$\mu$, a maximum pore size of 0.2$\mu$, and a void space of 38% was prepared.

This porous membrane was superposed on one side of the above-described drug-retaining layer followed by heat-pressing the assembly. Then, olive oil was coated on the porous membrane side to fill pores in the membrane with the olive oil. Thus, there was obtained a drug administration material of the present invention.

EXAMPLE 2

In the same manner as in Example 1, except for using fluocinolone acetonide as a drug and changing the drug content to 4 $\mu$g/cm$^2$, a drug administration material was obtained.

EXAMPLE 3

In a manner analogous to Example 1, except for using betamethasone valerate as a drug and changing the drug content to 2 $\mu$g/cm$^2$, a drug administration material was obtained.

EXAMPLE 4

In a manner analogous to Example 1, except for using betamethasone valerate as a drug and changing the drug content to 8 $\mu$g/cm$^2$, a drug administration material was obtained.

EXAMPLE 5

In the same manner as in Examples 1 to 4 except for using polypropylene glycol (grade: 3000) as a liquid filling pores of the porous membrane, drug administration material A (containing indomethacin), B (containing fluocinolone acetonide), C (containing dexamethasone), and D (containing betamethasone valerate) were obtained.

Carrageenin-induced paw edema-controlling ratio was measured with respect to the drug administration materials obtained in Examples 1 to 5 and with comparative drug administration materials not using the administration layers obtained in Examples 1 to 4 (comparative samples A, B, C and D).

The carrageenin-induced paw edema-controlling ratio was determined as follows.

Respective drug administration samples were applied to previously shaved backs of rabbits weighing 1.8 to 2.0 kg using an adhesive tape. After a predetermined period of time, the samples were delaminated, then applied to the backs of paws of Wister strain male rats (weighing 150 to 180 g). The samples were removed two hours after the application, and each of the rats was injected in subcutis of paw back with 0.3 $\mu$l of a 0.5% solution of carrageenin in a physical saline solution. Three hours after the injection, the volume of induced edema was measured with respect to each rat, with the volume of edema induced by injecting carrageenin into untreated rats being measured as a control. The edema-controlling ratio was calculated according to the following formula:

$$\text{Edema-controlling ratio (\%)} = \frac{V_s^2 - V_s^1}{V_c^2 - V_c^1} \times 100$$

wherein $V_s^2$ represents the volume of paws of sample-treated group rats, $V_s^1$ represents the volume of paws of the same rats before being treated with the samples, $V_c^2$ represents the volume of edema-induced paws of untreated rats, and $V_c^1$ represents the volume of paws of the untreated rats before the injection. The results thus-obtained are tabulated in Table 1.

TABLE 1

| | Time | | | | | | |
|---|---|---|---|---|---|---|---|
| | Initial Stage (%) | 2 Hrs (%) | 4 Hrs (%) | 8 Hrs (%) | 12 Hrs (%) | 16 Hrs (%) | 20 Hrs (%) |
| Example 1 | 35 | 38 | 36 | 35 | 35 | 33 | 28 |
| Example 2 | 47 | 46 | 45 | 48 | 44 | 32 | 21 |
| Example 3 | 28 | 35 | 33 | 38 | 36 | 36 | 33 |
| Example 4 | 36 | 38 | 33 | 35 | 37 | 34 | 20 |
| Example 5 | | | | | | | |
| A | 42 | 48 | 40 | 46 | 38 | 33 | 20 |
| B | 28 | 27 | 28 | 25 | 20 | 16 | 10 |
| C | 25 | 26 | 25 | 28 | 26 | 27 | 29 |
| D | 28 | 27 | 28 | 25 | 23 | 19 | 10 |
| Comparative Sample A | 26 | 10 | 3 | 3 | 5 | 4 | 0 |
| Comparative Sample B | 22 | 10 | 0 | 3 | 0 | 0 | 0 |
| Comparative Sample C | 30 | 18 | 10 | 0 | 3 | 2 | 0 |
| Comparative Sample D | 10 | 3 | 0 | 4 | 0 | 0 | 0 |

EXAMPLE 6

10 g of acrylic ester/acrylic acid copolymer (95:5 by weight) was mixed with 100 mg of phenobarbital, and the resulting mixture was coated on a 25μ thick polyethylene terephthalate film in a thickness of 50μ (content of phenobarbital; 50 μg/cm²) to prepare a drug-retaining layer.

Separately, a polyolefin-made porous membrane was prepared which had a thickness of 70μ, a maximum pore size of 0.3μ, and a void space of 70%, and polypropylene glycol (grade: 2000) or diisopropyl adipate was filled in the pores of the membrane to prepare two (A and B) administration layers.

The above-described drug-retaining copolymer layer was laminated on one side of each of the administration layer to obtain drug administration materials.

EXAMPLE 7

A 12μ thick polyethylene terephthalate film was laminated with rayon unwoven fabric having a b sic weight of 80 g/m², and the nonwoven fabric was impregnated with diazepam in an amount of 200 μg/cm² to obtain a drug-retaining layer.

On the drug-retaining surface was superposed the polyolefin-made porous membrane as used in Example 6 followed by heat-pressing. Then, olive oil was filled in the pores of the membrane to obtain a drug administration material.

EXAMPLE 8

A 2% solution of amobarbital in olive oil was filled in pores of a 60μ thick porous ethylene-polyvinyl alcohol membrane having a maximum pore size of 0.2μ and a void space of 120% to obtain a drug-retaining layer.

Separately, polyethylene glycol (grade: 600) was filled in the pores of the same porous membrane to prepare a drug administration layer.

Then, the drug-retaining layer was laminated on the drug administration layer to obtain a drug administration material.

Analgesic effects of the drug administration materials obtained in Examples 6 to 8 were measured according to a pressure-stimulating method using ddY strain mice. The results thus-obtained are given in Table 2.

TABLE 2

| | Time | | | | | |
|---|---|---|---|---|---|---|
| | Initial Stage (mmHg) | 0.5 Hrs (mmHg) | 1 Hrs (mmHg) | 2 Hrs (mmHg) | 4 Hrs (mmHg) | 8 Hrs (mmHg) |
| Example 6 | | | | | | |
| A | 30 | 45 | 55 | 50 | 53 | 35 |
| B | 33 | 60 | 76 | 74 | 78 | 38 |
| Example 7 | 31 | 76 | 85 | 78 | 81 | 62 |
| Example 8 | 34 | 40 | 42 | 38 | 41 | 36 |

While the invention has been described in detail and with reference to specific embodiments thereof, it will be apparent to one skilled in the art that various changes and modifications can be made therein without departing from the spirit and scope thereof.

What is claimed is:

1. A drug administration material for continuously administering an active drug at a controlled rate through an integument which comprises, in sequence, an adhesive film which comprises a film and a pressure sensitive layer, a barrier layer, a drug-retaining layer, a drug administration layer which continuously feeds an active drug to the integument, and a delaminatible protective film, said drug administration layer comprising a porous membrane containing in pores thereof, a liquid having a limited solubility for the active drug, wherein said liquid is stably retained in the porous membrane by capillary pressure.

2. A drug administration material as in claim 1, wherein said porous membrane has a pore diameter size of 10 μm or less.

3. A drug administration material as in claim 1, wherein the membrane comprises pores of a pore size of 0.01 to 5μ and has a void space of at least 70%.

4. A drug administration material as in claim 1, wherein the drug-retaining layer and the drug administration layer both contain active drug.

* * * * *